United States Patent [19]

Grassi et al.

[11] 4,423,733

[45] Jan. 3, 1984

[54] RELAY CIRCUIT FOR CARDIAC PACEMAKER IMPLANT

[76] Inventors: Gino Grassi, Via Imbriani 21, Sesto Fiorentino; Leonardo Cammilli, Via G. Caselli 11; Luciano Alcidi, Via G. Console 8, all of Firenze, Italy

[21] Appl. No.: 294,914

[22] Filed: Aug. 21, 1981

[51] Int. Cl.³ .............................................. A61N 1/36
[52] U.S. Cl. ............................................ 128/419 PG
[58] Field of Search .................. 128/419 PG, 419 PS, 128/419 PT

[56] References Cited

U.S. PATENT DOCUMENTS

| | | | |
|---|---|---|---|
| 4,088,139 | 5/1978 | Auerbach | 128/419 PT |
| 4,226,245 | 10/1980 | Bennett, Jr. | 128/419 PT |
| 4,228,803 | 10/1980 | Rickards | 128/419 PG |
| 4,305,396 | 12/1981 | Wittkampf et al. | 128/419 PG |

*Primary Examiner*—William E. Kamm
*Assistant Examiner*—Mitchell J. Shein
*Attorney, Agent, or Firm*—McAulay, Fields, Fisher, Goldstein & Nissen

[57] ABSTRACT

A relay circuit for a cardiac pacemaker having a stimulator implanted in a user. A first detector and a relay is involved for detecting and amplifying a cardiac wave, the first detector being capable of relaying the cardiac wave as a signal; a second detector and a relay is provided for detecting a stimulus signal of the stimulator of the pacemaker, the second detector being capable of relaying the stimulus signal; a cycle-to-cycle control receives signals from the first and second detectors for constructing a cycle-to-cycle wave signal of the cardiac and stimulus signals in accordance with a cardiac or physiological T wave and a stimulus R wave representation respectively of an electrocardiogram; a wave absence detector for detecting the absence of the cardiac wave or the stimulus wave in the cycle-to-cycle control, the wave absence detector being capable of relaying a wave absence signal; a receiver for receiving the wave absence signal and including a converter for translating the wave absence signal into a counteraction signal; and a counteractor for receiving the counteraction signal, including the provision of a signal for signaling a counteraction.

12 Claims, 4 Drawing Figures

RELAY CIRCUIT FOR CARDIAC PACEMAKER IMPLANT

BACKGROUND OF THE INVENTION

1. Field of the Invention

This invention relates to a relay for a cardiac pacemaker implant.

More particularly, the invention is concerned with a relay device for an implantable pacemaker which is used to generate signals to provide information regarding the cardiac pacemaker as well as for exciting auxiliary signalling circuits, circuits for reducing the frequency of stimulation, or for increasing the power and-/or the duration of a stimuli.

In general, a user or wearer of a cardiac pacemaker implant entrusts the vital functions of his or her heart to it. Any defect or malfunction of the cardiac stimulation of the pacemaker that would cause a continuous or even an intermittent failure of stimulation could endanger the health of the user to the point of imperiling survival.

2. Description of the Prior Art

Malfunction of an implanted pacemaker is due in most cases to defects in the stimulation electrode. Some examples of such defects include electrode displacement, perforation of the cardiac muscle by the electrode, reduced sensitivity due to incoming or outgoing current blockage, breakage of the electrode or circuit insulation, and breakage of the electrode itself. Such defects ggenerally are not subject to timely detection and often are discovered only incidently; such as for example, during a scheduled check of the pacemaker or a general cardiological examination. In any event, there is often a time lapse between the first occurrence of an anomaly and the detection of the pacemaker defect.

The ability to become cognizant of any variation from the correct functionary cycle of the pacemaker stimulation immediately upon occurrence of a malfunction is of the utmost importance. First, immediate detection would make possible an immediate counteraction to correct the operation at the implant itself, for example, by automatic switching to an auxiliary circuit provided for corrective purposes. Second, a signal to to the user of an anomalous operation that would warn the user of the deflect so that such user is aware of the problem and can report immediately to a medical control center to have the problem corrected.

Accordingly, it is an object of the invention to provide a relay circuit for use with a cardiac pacemaker to provide for the stimulation of a conventional cardiac pacemaker implant that acts as a circuit to control, signal, and aid in the operation of the pacemaker to which the relay circuit is connected.

It is another object of the present invention to provide a relay circuit for use with a cardiac pacemaker that will continuously compare that artifical stimuli generated by a pacemaker with signals derived from the activity of the heart muscle.

It is a further object of the present invention to provide a relay circuit for use with a cardiac pacemaker that effects a continuous examination of the output of every stimulation of a pacemaker.

SUMMARY OF THE INVENTION

To these ends, the invention consists in the provision of a relay circuit for generating an electrical signal for an implantable cardiac pacemaker responsive to T waves which are characteristic of physiological waves and R waves characteristic of wave ventricular stimulation, and comprises a cycle-by-cycle control responsive to the effects produced by the electric stimulation of the cardiac pacemaker for detecting the beginning of the absence of a response from the heart muscle, due to the absence of one of the T waves for the generation of the electric signal, which are diversely utilized, such as for exciting auxiliary signaling circuits, circuits reducing the frequency of stimulation, or increasing the power and duration of the stimuli.

Two related embodiments of relay circuit are provided. The operation of each embodiment is based upon the detection of the presence or absence of the physiological cardiac wave, that is, the electrical T wave of an electrocardiagram, or of a pacemaker stimulator, and the R wave of the ventricular stimulation. It is understood that the two forms of the invention presented are for purposes of illustration only and are not intended to limit the scope of the present invention.

In one preferred embodiment, an adder circuit is used which is responsive to the output of a chain of circuits formed by an amplifier, a pulse generator and a bistable multivibrator which processes the signal derived from the cardiac activity, and a second signal derived from a first monostable multivibrator which is synchronized directly by the pulses of the pacemaker. Further, the adder provides a comparison between the pulses furnished by the bistable multivibrator and pulses from the first monostable multivibrator, and a second bistable multivibrator provides a signal which is fed to the pacemaker to provide signals carrying information relative to the appearance of one or more stimuli which are not followed by ventricular stimulation.

In another embodiment, a bistable circuit is successively synchronized in each period of a cardiac cycle by the stimulation pulse and by a pulse generated by a pulse forming circuit coupled to an amplifier which amplifies the T waves concordant with the wave of the intracavitary signal so that any irregularity in the switching of the aforesaid bistable circuit due in particular to the absence of the cardiac wave in the cycle, is reported to the pacemaker, which is appropriately programmed for the purpose. An auxiliary signaling circuit is arranged to evidence and signal to the implant wearer that there is a block due to a loss of stimulation.

Other objects, advantages and the nature of the invention will become readily apparent from the detailed description of the preferred modes of carrying out the invention described in connection with the accompanying drawings.

DETAILED DESCRIPTION OF THE INVENTION

Figure 1:
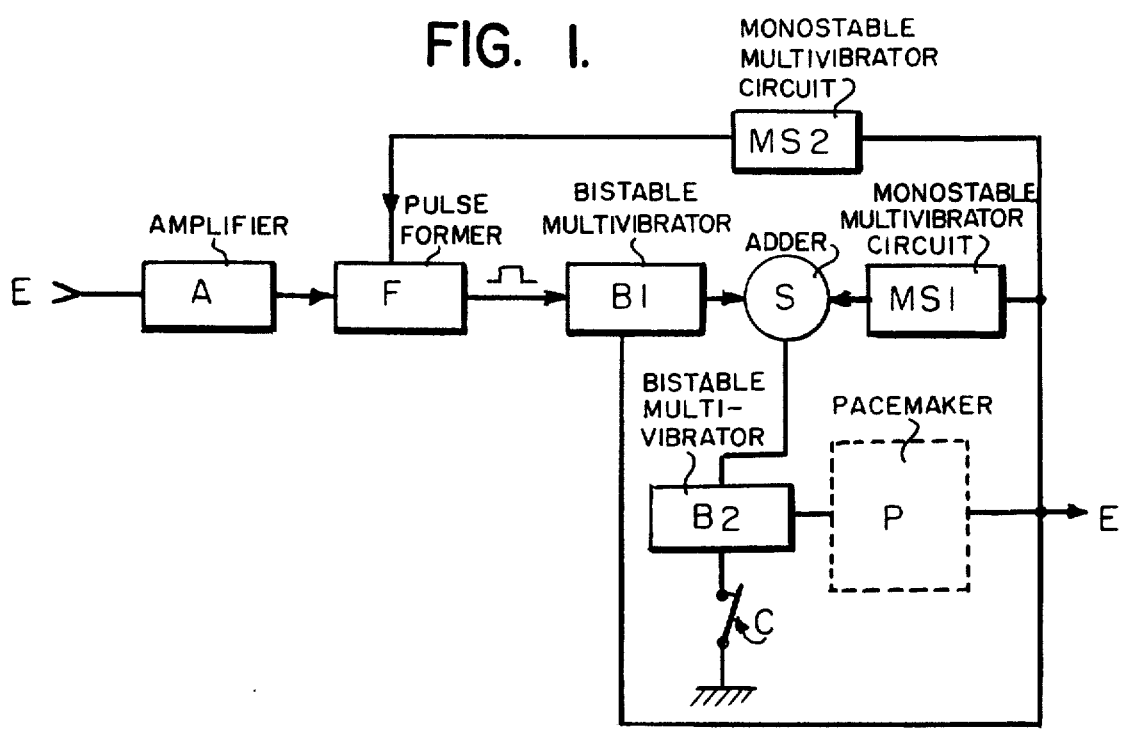
FIG. 1 is a schematic representation of one embodiment of the invention illustrated in a block diagram form of the relay circuit of the invention in combination with a conventional pacemaker.

Referring now more particularly to FIG. 1 of the drawings, a conventional pacemaker P (shown in dotted outline) is schematically shown in combination with one form of relay circuit according to the invention.

The relay circuit according to the invention comprises an amplifier A having an input from electrode E which is derived from the output of an intercavity signal indicating cardiac activity, a pulse generator or former F having one input connected to the output of amplifier A, two bistable multivibrator circuits B1 and B2, two monostable multivibrator circuits MS1 and MS2, an adder S and a resetting contact circuit C connecting the bistable multivibrator circuit B2 to a source of reference potential. Pulse former F has two inputs, one from the output of amplifier A and the other from the monostable multivibrator MS2. The output of pulse former F is applied to the bistable multivibrator circuit B1. The output of the pacemaker P is capable of supplying stimulation impulses T and this is applied to the monostable multivibrator MS1, monostable multivibrator MS2 as well as electrode E and bistable multivibrator circuit B1. The outputs of bistable multivibrator circuit B1 and monostable multivibrator circuit MS1 are then applied to adder S and the output of adder S is applied to the bistable multivibrator circuit B2. The output of bistable multivibrator circuit B2 is applied to the pacemaker P for the control thereof, and the resetting contact circuit C is schematically shown as a normally open switch which when closed resets the bistable multivibrator B2.

Figure 2:
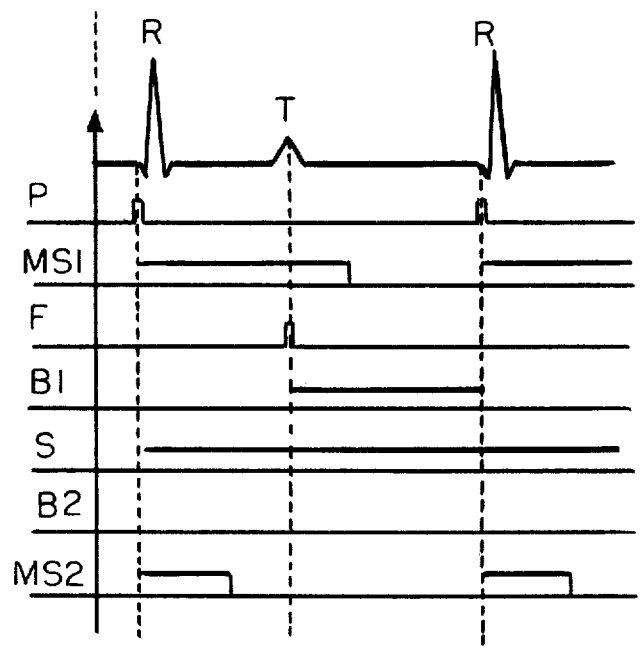
FIG. 2 illustrates a cycle-to-cycle diagram of the operation of the relay circuit of FIG. 1 according to the R wave which signifies ventricular stimulation because of the absence of a physiological cardiac wave and the T wave which indicates the presence of a physiological cardiac wave of a wave diagram of an electrocaridogram taken of a person with a pacemaker implant.

FIG. 2 illustrates an electrocardiogram wave form composed of normal heart beats and pacemaker stimulation impulses. Specifically, the electrocardiogram wave form shows the R wave which includes the spike of the pacemaker cardiac stimulation and the T wave or spike which is a representation of the heart muscle in the stasis state (stable state). With reference to FIGS. 1 and 2, the relay circuit operates as follows: amplifier A amplifies the intracavitay, or cardiac signal from electrode E, which orignates with the physiological heart wave and is picked up by the input to amplifier A from the output of electrode E to which the output of pacemaker P is connected, and the signal is of a sufficient level to activate pulse forming circuit F. The latter, in accordance with the T wave or spike of the signal, furnishes a square wave pulse to bistable multivibrator circuit B1, thereby causing the immediate and rapid switching of bistable multivibrator circuit B1.

At the beginning of the cardiac cycle, bistable multivibrator B1 is switched off to a non-signal phase by the effect of the impulse made by stimulation signal R from pacemaker P. The signal sent by pacemaker P is received by monostable circuit MS2, which in turn is applied to pulse former F and signals pulse former F to make it non-susceptable to a signal characteristic of ventricular stimulation R and to cease the signal in B1 triggered by the cardiac wave T or heart muscle in the stable or stasis state.

The stimulation signal in accordance with wave R sent by pacemaker P is also received by the monostable multivibrator MS1, which is activated to start a signal that MS1 maintains for a somewhat longer time than the interval between the start of the signal at the R wave, or ventricular stimulation spike, and the physiological T wave of the electrocardiogram.

Adder circuit S receives and adds signals sent to it by bistable multivibrator B1, and monostable multivibrator MS2 with the results that under normal cycle conditions—that is, where both the pacemaker cardiac stimulus wave R and the cardiac complex wave T are present—bistable multivibrator B2 is activated with a continuous signal of constant level signal from adder S. If the T wave is absent from the cycle, indicating stasis of the heart muscle, adder circuit S lacks the contributing signal furnished by bistable multivibrator B1 with the result that bistable multivibrator B2 is switched by the resetting contact or switch C to signal pacemaker P. Also, if adder S lacks the contributing signal from MS1 indicating a malfunction of the stimulus from the pacemaker P, bistable multivibrator B2, is likewise switched by resetting contact C and to signal pacemaker P. Any signal indicating a change of state of bistable multivibrator B2 indicates either the presence of stimuli not followed by the ventricular complex T or the lack of stimuli from the pacemaker and is usable by the pacemaker for activating auxiliary circuits (not shown) and for signaling the user if the anomaly is encounted via switch C.

It is noted that the circuit shown in FIG. 1 between bistable multivibrator B1, and pacemaker P is for the purpose of signaling pacemaker P of the cardiac signal so that the subsequent stimulus signal from pacemaker P may be sent to the heart via the output thereof to the electrode E.

Figure 3:
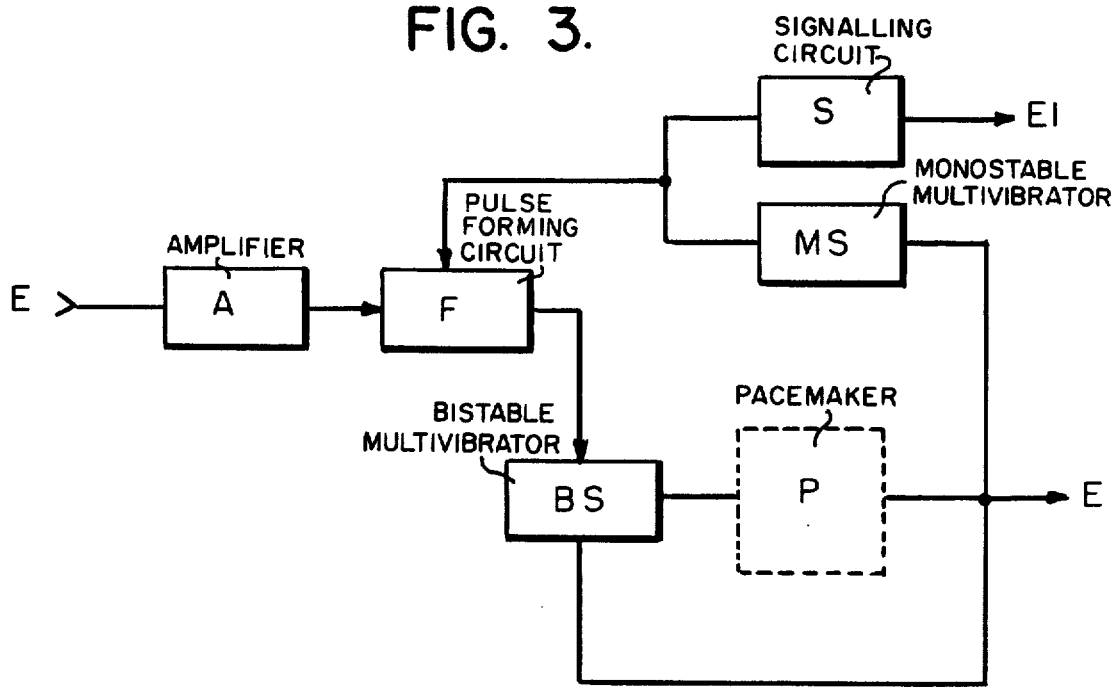
FIG. 3 is a schematic representation of another embodiment of the invention shown in block form of the relay circuit of the invention in combination with a conventional pacemaker.

Referring now more particularly to FIG. 3 which illustrates another circuit relay construction according to the invention and shows an amplifier A connected to electrode E so as to pick up the cardiac wave and to a pulse forming circuit F, a monostable multivibrator MS, a bistable multivibrator BS, a pacemaker P for producing an output stimulus which is applied to electrode E and a signaling circuit with a warning electrode implant E1.

Figure 4:
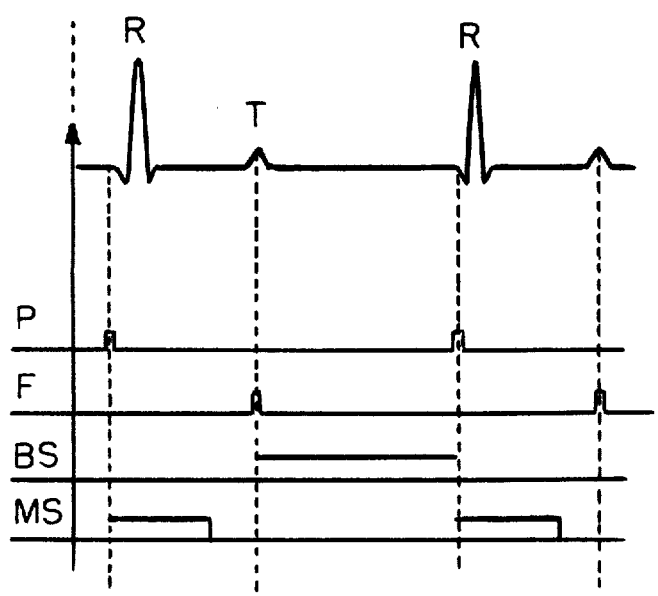
FIG. 4 illustrates a cycle-to-cycle diagram of the operation of the relay circuit of FIG. 3 illustrating the R wave and the T wave of a wave diagram of an electrocardiogram.

The operation is as follows: pulse former F is synchronized by the intracavitary signal previously amplified by amplifier A to send out a pulse in accordance with physiological cardiac wave T. The operation is inhibited from sending out a signal by the arrival of the R wave of ventricular stimulation from pacemaker P to activate monostable multivibrator MS, and by action of monostable multivibrator MS to control pulse former F, which after triggering bistable multivibrator BS to deactivate, automatically ceases operation before the arrival of the next T wave in the cycle. During a normal cycle, bistable multivibrator BS receives the pulse generated by the cardiac wave and shows continuous signal according to the electrocardiogram illustrated as the first wave form of FIG. 4 until the signal ceases by inhibition originating with the pacemaker cardiac stimulus signal which causes a change in state in bistable multivibrator BS.

The absence of the R wave is reported by a second circuit to pacemaker P by the failure of the bistable multivibrator BS to return to its state of rest and is transmitted by the pacemaker via an auxiliary circuit connecting the output of the pacemaker P with bistable multivibrator BS into supplying a stimulus of greater energy than conventional.

Stimultaneously, the absence of the T wave is detected by signaling circuit S, which warns the user by means of a secondary muscular stimulation directed to electrode implant E1. The signaling circuits can also function to warn of the absence of the R wave or stimulation impulse.

It is noted that the second circuit shown in FIG. 3 between bistable multivibrator BS and the junction of the circuit between P and E is for the purpose of signaling P of the lack of occurrence of the cardiac wave so that the subsequent stimulus signal from P may be sent to the heart via electrode E.

In summary, there is provided a relay circuit for a cardiac pacemaker having a stimulation implanted in a user, comprising a first detector and relay means for detecting and amplifying a cardiac wave, the first detector means being capable of relaying the cardiac wave as a signal; a second detector and relay means for detecting a stimulus signal of the stimulator of the pacemaker, the second detector means being capable of relaying the stimulus signal; cycle-to-cycle control means for receiving signals from the first and second detector means and for constructing a cycle-to-cycle wave signal of the cardiac and stimulus signals in accordance with a cardiac or physiological T wave and a stimulus R wave representation respectively of a electrocardiogram; wave absence detection means for detecting the absence of the cardia wave or the stimulus wave in the control means, the wave absence detection means being capable of relaying a wave absence signal; receiving means for receiving the wave absence signal, including means for translating the wave absence signal into a counteraction signal; and counteraction means for receiving the counteraction signal, including means for signaling a counteraction and means to impliment the counteraction.

It is obvious that various changes and modifications may be made herein without departing from the scope of the invention. In particular, either a physiological R wave or an R wave of ventricular stimulation or the physiological T wave could be used as a basis on which to create a counteraction signal within the scope of the invention.

While there has been shown and described what is considered to be the preferred modes of carrying out the invention, it will be obvious to those skilled in the art that various changes and modifications may be made therein without departing from the scope of the invention.

We claim:

1. A relay circuit for a cardiac pacemaker having a stimulator implanted in a pacemaker user, comprising:
    first relay means for amplifying a detected cardiac wave, said first relay means being capable of relaying a signal characteristic of said cardiac wave,
    second relay means for relaying a signal characteristic of a stimulus impulse of said stimulator of said pacemaker
    cycle-to-cycle control means for receiving said characteristic signals from said first and said second relay means and for constructing a cycle-to-cycle wave signal characteristic of a cardiac T wave and a stimulus R wave representation respectively of an electrocardiogram,
    wave absence detection means for detecting the absence of said cardiac wave or said stimulus impulse in said cycle-to-cycle control means, said wave absence detection means being capable of relaying a wave absence signal, and
    means for receiving said wave absence signal including means for translating said wave absence signal into a counteraction signal, and
    means for receiving said counteraction signal including means for signaling a counteraction, and means to implement the counteraction.

2. A relay circuit as claimed in claim 1, wherein said cycle-to-cycle control means is an adder circuit for adding said signal characteristic of the cardiac wave and said signal characteristic stimulus impulse to form said cycle-to-cycle wave signal.

3. A relay circuit as claimed in claim 2, wherein said first relay means includes a cardiac wave amplifier, a cardiac wave pulse former, and a first bistable multivibrator circuit, said amplifier being capable of receiving a cardiac wave signal for amplification thereof and of sending an amplified cardiac wave signal to said wave former, said wave former being capable of receiving said amplified cardiac wave signal and of forming said signal and of sending a cardiac wave form signal to said first bistable circuit, said first bistable circuit being capable of generating said signal characteristic of said cardiac signal and for relaying thereof to said adder circuit; and wherein said second relay means includes a first monostable multivibrator capable of receiving a stimulus signal form said stimulator and of forming said signal characteristic of said stimulus impulse and sending thereof as a simultaneous deactivation signal to said first bistable circuit through said pulse former, and a second monostable multivibrator capable of receiving said stimulus impulse from said stimulator and of sending said signal characteristic of said stimulus impulse to said adder circuit.

4. A relay circuit as claimed in claim 3, wherein said wave absence detection means includes a second bistable multivibrator circuit for receiving a continuous cycle-to-cycle wave signal form said adder circuit during a normal cycle and for detecting the absence of either said cardiac wave or said stimulus wave and of relaying said wave absence signal to said receiving means.

5. A relay circuit as claimed in claim 4, wherein said means for receiving said wave absence signal includes means coupled to the output of said second bistable multivibrator, and said means for receiving said counteraction signal includes an electrode coupled to the output of a pacemaker implanted in said user associated with said second bistable multivibrator capable of warning said user by a secondary muscular stimulation.

6. A relay circuit as claimed in claim 5, wherein said pacemaker is capable of receiving a signal from said second bistable circuit and said means for receiving a counter-action signal includes an auxiliary circuit, means being provided for signaling said auxiliary circuit to activate it upon receipt of said wave-absence signal, said auxiliary circuit being capable of duplicating the action of said stimulator of said pacemaker.

7. A relay circuit as claimed in claim 1, wherein said cycle-to-cycle control is a control bistable multivibrator capable of activation upon receipt of a signal from said first relay means and of deactivation upon receipt of a deactivation signal from said second relay means.

8. A relay circuit as claimed in claim 7, wherein said first relay means includes a cardiac wave amplifier, and a cardiac wave pulse former, said amplifier being capable of receiving a cardiac wave signal and amplifying said signal and of sending said amplified cardiac wave signal to said wave former, said wave former being capable of receiving said amplified cardiac wave signal and of forming said signal and of sending a cardiac wave form signal as a signal characteristic of the cardiac wave to said control bistable multivibrator; and wherein said second relay means includes a monostable multivibrator capable of receiving a stimulus signal from said stimulator and to relay said signal characteristic of said stimulus impulse as a deactivation signal to said control bistable multivibrator.

9. A relay circuit as claimed in claim 8, wherein said wave-absence detection means and said receiving means is a pacemaker circuit contained in said pacemaker, said pacemaker circuit being capable of detecting the absence of a cardiac wave.

10. A relay circuit as claimed in claim 9, wherein said counter-action means includes a means for generating a pacemaker stimulus signal of greater energy than normal.

11. A relay circuit as claimed in claim 10, wherein said, counter-action means further includes a signaling circuit being capable of receiving a wave-absence signal from said pacemaker circuit and of sending a simultaneous signal to said electrode implant.

12. A relay circuit for a cardiac pacemaker as claimed in claim 8, having a warning electrode implanted in the user, including a signaling circuit coupled to the output of said monostable multivibrator for signaling said circuit and said warning electrode of the presence of the signal characteristic of said stimulus impulse and the absence of the signal characteristic of the cardiac wave.

* * * * *